US011969405B2

(12) United States Patent
Sajic et al.

(10) Patent No.: US 11,969,405 B2
(45) Date of Patent: Apr. 30, 2024

(54) METHOD OF TREATMENT OF TOPICAL DERMATOLOGIC ACNE USING A CREAM COMPOSITION AND METHOD OF MANUFACTURE

(71) Applicant: DERMA RESEARCH GROUP INC., Guelph (CA)

(72) Inventors: Dusan Sajic, Puslinch (CA); Maksym Breslavets, Toronto (CA); Scottpatrick Sellitto, Buffalo, NY (US)

(73) Assignee: Derma Research Group, Inc., Guelph (CA)

( * ) Notice: Subject to any disclaimer, the term of this patent is extended or adjusted under 35 U.S.C. 154(b) by 0 days.

(21) Appl. No.: 17/901,688

(22) Filed: Sep. 1, 2022

(65) Prior Publication Data
US 2023/0055512 A1 Feb. 23, 2023

Related U.S. Application Data

(63) Continuation of application No. 16/742,595, filed on Jan. 14, 2020, now abandoned.
(Continued)

(51) Int. Cl.
| | | |
|---|---|---|
| A61K 31/327 | (2006.01) | |
| A61K 9/00 | (2006.01) | |
| A61K 9/06 | (2006.01) | |
| A61K 31/045 | (2006.01) | |

(Continued)

(52) U.S. Cl.
CPC .......... *A61K 31/327* (2013.01); *A61K 9/0014* (2013.01); *A61K 9/06* (2013.01);
(Continued)

(58) Field of Classification Search
CPC .................................................... A61K 31/327
See application file for complete search history.

(56) References Cited

U.S. PATENT DOCUMENTS

| | | |
|---|---|---|
| 7,198,807 B2 | 4/2007 | Anderson et al. |
| 7,727,562 B2 | 6/2010 | Blackman |

(Continued)

FOREIGN PATENT DOCUMENTS

| | | |
|---|---|---|
| BR | 102017003316 A2 | 10/2018 |
| WO | WO-2012013776 A2 | 2/2012 |

*Primary Examiner* — Benjamin J Packard
(74) *Attorney, Agent, or Firm* — Cherskov Flaynik & Gurda, LLC (57) ABSTRACT

In some aspects, the techniques described herein relate to a topical dermatologic acne treatment method using a cream. The treatment method uses two steps, first providing a bactericidal component and second providing a skin revitalizing complex. The bactericidal component clears the acne causing bacteria. The subsequent skin revitalizing complex revitalizes and conditions the skin and aids in return of natural skin flora and microbiome to prevent subsequent outbreaks. The skin revitalizing complex can include a variety of components such as: niacinamide, retinol, bakuchiol, green coffee bean extract, green tea extract, epilobium fleischeri extract, citric acid, dimethicone, and pentaerythrityl tetracaprylate. The skin revitalizing complex restores natural elasticity and oil production of the skin, decrease sebum production, and provide necessary conditioning of the skin to provide for the natural skin flora and microbiome to repopulate and flourish on a surface of the skin.

21 Claims, 3 Drawing Sheets
(3 of 3 Drawing Sheet(s) Filed in Color)

Related U.S. Application Data (60) Provisional application No. 62/792,809, filed on Jan. 15, 2019.

(51) Int. Cl.

| | |
|---|---|
| *A61K 31/05* | (2006.01) |
| *A61K 31/095* | (2006.01) |
| *A61K 31/145* | (2006.01) |
| *A61K 31/194* | (2006.01) |
| *A61K 31/25* | (2006.01) |
| *A61K 31/455* | (2006.01) |
| *A61K 31/65* | (2006.01) |
| *A61K 31/7048* | (2006.01) |
| *A61K 31/7056* | (2006.01) |
| *A61K 33/30* | (2006.01) |
| *A61K 36/185* | (2006.01) |
| *A61K 36/58* | (2006.01) |
| *A61K 36/61* | (2006.01) |
| *A61K 36/74* | (2006.01) |
| *A61K 36/82* | (2006.01) |
| *A61K 47/34* | (2017.01) |
| *A61P 17/10* | (2006.01) |

(52) U.S. Cl.
CPC ............ *A61K 31/045* (2013.01); *A61K 31/05* (2013.01); *A61K 31/095* (2013.01); *A61K 31/145* (2013.01); *A61K 31/194* (2013.01); *A61K 31/25* (2013.01); *A61K 31/455* (2013.01); *A61K 31/65* (2013.01); *A61K 31/7048* (2013.01); *A61K 31/7056* (2013.01); *A61K 33/30* (2013.01); *A61K 36/185* (2013.01); *A61K 36/58* (2013.01); *A61K 36/61* (2013.01); *A61K 36/74* (2013.01); *A61K 36/82* (2013.01); *A61K 47/34* (2013.01); *A61P 17/10* (2018.01)

(56) References Cited

U.S. PATENT DOCUMENTS

| | | |
|---|---|---|
| 7,737,181 B2 | 6/2010 | Graeber et al. |
| 9,713,596 B2 | 7/2017 | Hong et al. |
| 2005/0255133 A1 | 11/2005 | Schwarz et al. |
| 2007/0207115 A1 | 9/2007 | Liegeois |
| 2011/0250227 A1 | 10/2011 | Elraz |
| 2011/0305747 A1 | 12/2011 | Ahluwalia et al. |
| 2011/0318434 A1 | 12/2011 | Guthery |
| 2012/0258177 A1 | 10/2012 | Goldstein et al. |
| 2014/0147396 A1* | 5/2014 | Sertchook ............ A61K 9/1075 424/59 |
| 2015/0126759 A1 | 5/2015 | Boaz et al. |
| 2016/0008295 A1 | 1/2016 | Tseng et al. |
| 2017/0119703 A1 | 5/2017 | Warner et al. |

* cited by examiner

METHOD OF TREATMENT OF TOPICAL DERMATOLOGIC ACNE USING A CREAM COMPOSITION AND METHOD OF MANUFACTURE

The instant application claims priority as a continuation of U.S. application Ser. No. 16/742,595, filed on Jan. 14, 2020, which in turn claimed priority to U.S. Provisional Application 62/792,809 filed on Jan. 15, 2019. The contents of each of which are hereby incorporated by reference.

FIELD OF THE INVENTION

This invention relates to topical cream composition for the treatment of acne vulgaris. More specifically, this invention relates to a multi-element composition wherein the individual elements operate in conjunction and synergistically to: 1. eliminate or reduce the presence of pathogenic acne vulgaris and associated inflammation; and 2. revitalise and recondition the skin to prevent subsequent outbreaks of acne vulgaris. Furthermore, the invention relates to the method of manufacture the topical cream composition through a multi-step process wherein the topical cream is made in a two-step process thereby making it adaptable to a variety of indications beyond acne vulgaris.

The invention also relates to the creation of a skin revitalizing compound which revitalises and reconditions the skin. The skin revitalizing compound can be used in association with a variety of active ingredients for a variety of different skin indications. As the multi-step method of manufacture allows for the separation of the clinically active vase from other disease specific ingredients the skin revitalizing compound is adaptable to a variety of indications beyond acne vulgaris.

BACKGROUND

Acne Vulgaris (also referred to as the "skin disease') is the most common skin disease, affecting to some degree ninety percent (90%) of all individuals as they mature through puberty. The skin disease persist in a large portion of this individuals well past puberty, affecting many adults for extensive periods of time. It is also not uncommon for adults to develop the skin disease for the first time in their early to late thirties.

The skin disease is a pleomorphic skin disease characterised by open comedones (or "blackheads"), closed comedones (or "white heads"), inflammatory papules, pustules, cysts and various sized nodules and scars. Inflammation often occurs with the disease, which is indicative of bacterial skin contamination and/or infection. The disease involves the pilosebaceous units of the dermis which consist of the hair follicle, follicular ostium and sebaceous gland. Multiple factors (or "causes") are involved in the skin disease's inception and numerous studies have shown that targeting any one of the factors can improve the appearance of the skin and alleviate some of the observable effects caused by skin disease. While the approach of targeting one factor of cause is helpful, the inability to target all of the causes involved has led to therapies that are suboptimal.

There are many causes of the skin disease including but not limited to the change of the bacterial flora on the skin and general microbiome, increased sebum production, hyperkeratinisation of the pilosebaceous unit, and inflammation. The skin flora and the microbiome composition are additional causative agents to the formation of the skin disease. Overgrowth of *Propinobactreium Acnes*, or reduction of beneficial bacteria have both been shown to increase the severity of the skin disease and lead to increasing current treatment failure. In addition, the air quality of the environment and general cleanliness and maintenance of the skin play very important factors in the progression of the skin disease. The skin elasticity, and oil expression are additional contributors to general skin health and homeostasis.

Another commonly described cause of acne vulgaris is the result of the clogging of the follicular canals on the skin. Clogging is often as a result of particles, such as dead skin layers, also known as keratin, breaching the mouth of the follicular canal and interacting with an accumulation of sebum. The clogged follicular canal results in inflammation that is manifested on the surface of the skin as pustules, cysts, nodules, granulomatous reactions scars, and might even cause the development of keloids. Pustules and papules can heal with scar formation, fibrosis of the lesions which are deep and penetrating. Clogging can also result from the excessive production and flow of seabum from the sebaceous glands. Seabum reaches the skin surface through the duct of the hair follicle. The presence of excessive amounts of sebum in the duct and in the skin acts to block the continuous flow of sebum from the duct, thereby producing a thickening that is defined as comedone that closes the duct.

The causes of the skin disease described, are also common in a wide variety of skin conditions.

There are a number of acne compounds currently available in the over the counter market for the treatment of acne vulgaris. These marketed products usually employ one or two active ingredients that target one more two of the above pathways that lead to the skin disease. Many of the acne compounds contain a bactericidal or an antibiotic active element to eliminate the bacteria that may cause acne vulgaris. The commonly used bactericidal active elements for the treatment of the skin disease include Benzoyl Peroxide ("BPO") and Salicylic Acid. These are great bactericidal elements but, as provided by the marketed compounds, are not effective in eliminating the skin disease.

While these active elements are great bactericidal elements, they currently available marketed compounds have been suboptimal at reducing the skin disease. The main deficiency in the current compounds relates to the manner in which the bactericidal elements penetrate the skin and maintain their stability. Most current compound place the BPO on the surface of the skin. This is not an effective means of eliminating the skin disease causing bacterial because the bacteria are not only found on the surface of the skin but also reside within the deeper sebaceous gland, which is below the surface. Application of the BPO or salicylic acid on the surface of the skin is ineffective at eradicating the acne vulgaris causing bacteria, as the bacteria within the sebaceous gland is not affected. Furthermore, stability of BPO and salicylic acid is often compromised by the additional elements that are found in the acne compounds currently available on the market. Finally, the use of BPO alone does not address the status of the skin, the flora and the microbiome once the bactericidal action of BPO has impacted the flora and the microbiome while drying out the skin.

Another current approach for the treatment of acne vulgaris include the use of prescription-based antibiotics—either as a topical cream or taken orally, combined oral contraceptives, antiandrogen medications, and oral Isoterinoine. The use of prescription antibiotics is quickly losing favour within the medical community, as they only provide temporary relief of the disease (while being used) and also lead to the increasing problem of increasingly virulent antibiotic resistant bacterial strains. Furthermore, the use of antibiotics targets indiscriminately beneficial bacteria as well. Indeed, as with over the counter marketed topical creams, the use of antibiotics alone does not address the status of the skin, the flora and the microbiome once the antibacterial action has impacted the flora and the microbiome. The use of combined oral contraceptives, antiandrogens, and Isotertinoine is often not a first choice due to side effect profile and associated risks.

Various attempts have been made to eliminate or reduce acne formation through the elimination of all bacterial cultures from the surface of the skin. Prior publications such as U.S. Pat. No. 5,505,949 (Benitez); U.S. Pat. No. 6,433,024 (Popp); and, U.S. Pat. No. 4,446,145 (Van Bever) provide such examples for the use of bactericidal and antibiotic elements for the treatment of acne vulgaris.

Benitez discloses a topical acne cream having primary ingredients such as: an antifungal ingredient, anti-inflammatory ingredient; and an anti-septic/anti-bacterial/keratolytic substance. The topical acne cream is also comprised of secondary ingredients such as binders, emulsifiers and fillers. The active ingredients compose of mutually potentiating amounts of BPO and of at least one chemical compound of an azole derivative and a therapeutically active non-toxic acid. The focus in Benitez is the antibacterial properties of the topical acne cream as evidence by the in vitro clearing of bacterium that may be recovered from skin-lesions caused by acne vulgaris. Benitez employs various antibacterial elements, such as antibiotics, bactericidal, and anti-fungal to reduce acne vulgaris. These elements are used in conjunction through the aid of binders, fillers, and emulsifiers as physiological support that stabilize the topical acne cream and prolong storage. Benitez, therefore, is primarily focused on bacterial killing agents but fails to recognize the need for novel elements that rejuvenates and conditions the skin and fails to recognize the need to repopulate the natural, non-acne vulgaris causing, bacteria, in addition to the general flora and microbiome of the skin. These novel elements aid in preventing the reoccurrence of acne vulgaris after initial clearing.

Popp discloses a topical composition for the treatment of acne comprising of water, an organic peroxide, an alpha hydroxyl acid, a moisturizer, an isosorbide and a detergent. The invention in Popp relates to the use of BPO composition which combines the desired anti-acne properties with the desired non-irritating properties of cream-like formulation. Popp focuses on a cream that is less irritating or perceived to be less irritating than compositions in the prior art, as BPO is known to be an irritant. Popp fails to recognize that the irritation of BPO is dramatically reduced when BPO is localized within the skin at a depth of the sebaceous glands. Furthermore, Popp fails to prevent the subsequent outbreaks of acne vulgaris through the rejuvenation and conditioning of the skin that encourages the regrowth of the natural, non-acne vulgaris causing, bacterial flora of the skin thereby repopulating the natural microbiome of the skin.

Van Bever discloses a topical treatment of acne vulgaris comprising a pharmaceutically acceptable amount of BPO and an anti-microbially effective amount of a suitable azole derivative. Van Bever focuses on clearing the skin of bacteria and fungus that is responsible for the emergence of acne vulgaris. The invention of Van Bever employs BPO for clearing of bacteria and azole for the clearing of fungi on the skin surface. What Van Bever fails to recognize acne has multiple causes, of which bacterial and fungal infection a small proportion. Furthermore, Van Bever fails to prevent future outbreaks of acne vulgaris by rejuvenating and reconditioning the skin and ensuring the regrowth of non-acne vulgaris causing bacterial flora and establishing the healthy skin microbiome.

As such, there is a need for an acne treatment cream that has a multifaceted mode of action, of which, only one element causes the clearing of acne vulgaris causing bacteria through BPO. A system that not only provides for a stable and non-interacting BPO that penetrates to the correct depth of the skin, but also helps aid with the general health of the skin. A system that rejuvenates the skin, normalize sebum production and keratinization, retains the skin elasticity, minimizes follicle pore diameters and creates an environment conducive to the regrowth of beneficial skin bacterial flora. A system that reopens follicular canals once they have become closed and can act against the thickening sebum. There is need for a skin cream that also reduces the formation of scarring and subsequent reduction in previously acquired acne lesion.

SUMMARY

The present invention provides a topical cream composition for the use in dermatologic acne treatment of infected skin. The topical dermatologic acne treatment cream through a two-stage process: the clearing the acne currently present on the skin; and reducing the potential reoccurrence of additional acne. The clearing of the presenting acne is accomplished through the use of an acne bactericidal. The reducing the potential reoccurrence of additional acne is accomplished through a skin revitalizing compound that returns the skin to its natural homeostasis thereby encouraging the regrowth of natural, non-acne vulgaris causing, bacterial flora of the skin. In addition, the topical dermatologic acne treatment cream normalizes the keratinization process and decreases the production of sebum from the pilosebaceous unit. The present invention also provides for a method of manufacture the Topical Dermatologic Acne Treatment Cream through two-stage process wherein the bactericidal is added to the skin revitalizing compound. The skin revitalizing compound can be used as a secondary element to various skin conditions or on its own to maintain the general health and skin condition.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

It will now be convenient to describe the invention with particular reference to one embodiment of the present invention. It will be appreciated that the drawings relate to one embodiment of the present invention only and are not to be taken as limiting the invention.

DETAILED DESCRIPTION

Figure 1:
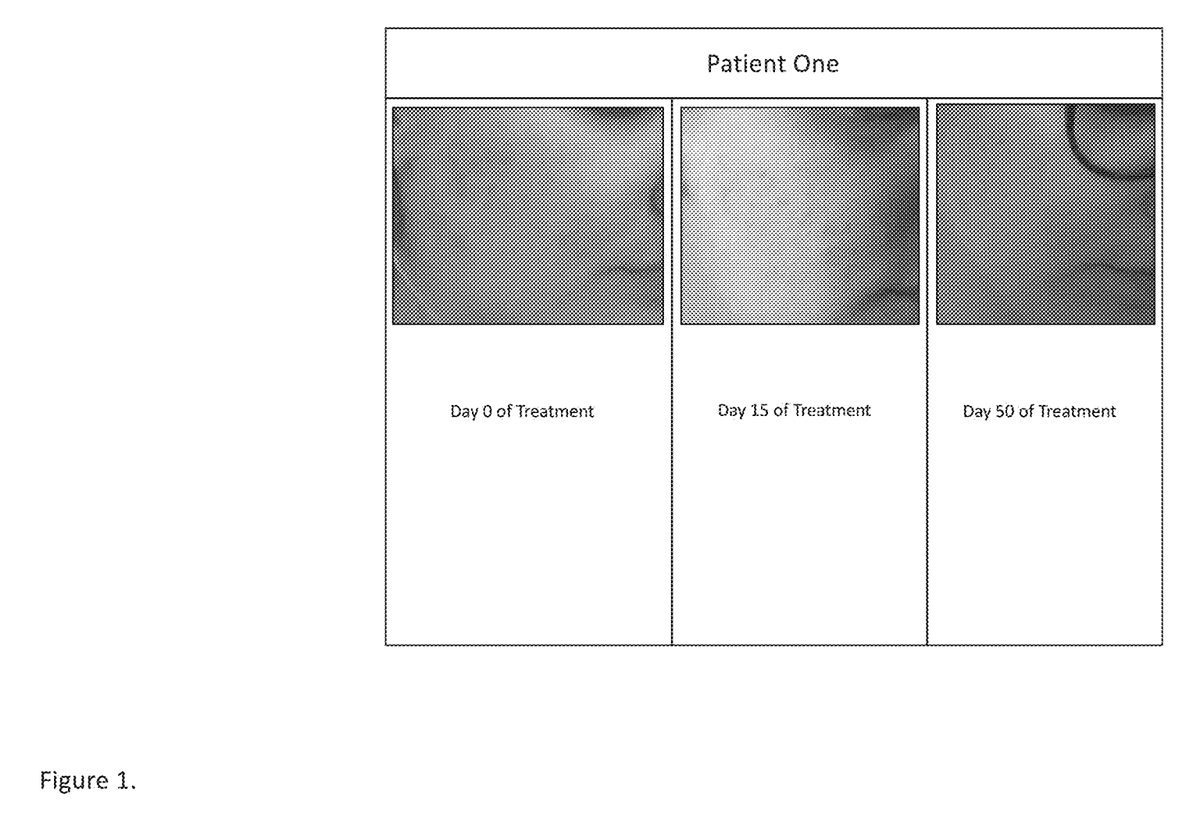
FIG. 1 is an image of the right cheek of Patient One at time points: day 0; day 15; and, day 50; post initial day of treatment of the Topical Dermatologic Acne Treatment applied twice a day, shown consecutively from left to right, according to one embodiment of the present invention.
Figure 2:
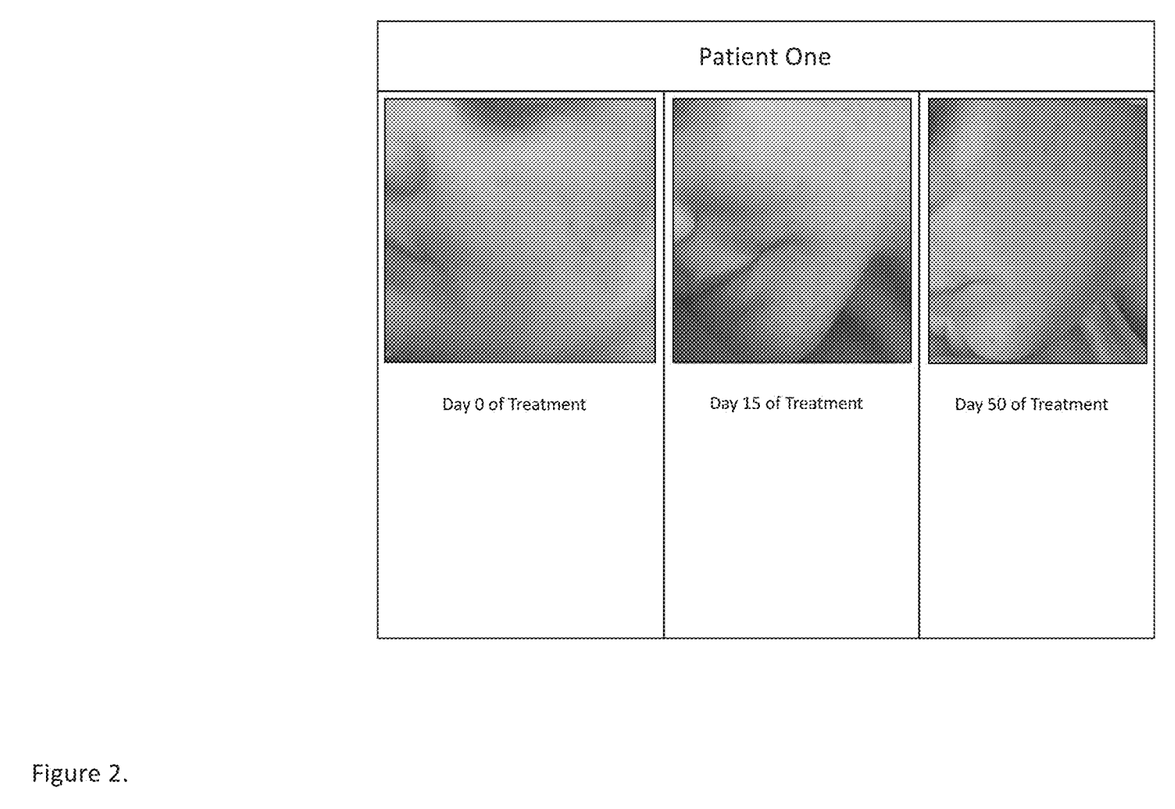
FIG. 2 is an image of the left cheek and left chin of Patient One at a time points: day 0; day 15; and, day 50; post initial day of treatment Topical Dermatologic Acne Treatment applied twice a day, shown consecutively from left to right, according to one embodiment of the present invention.
Figure 3:
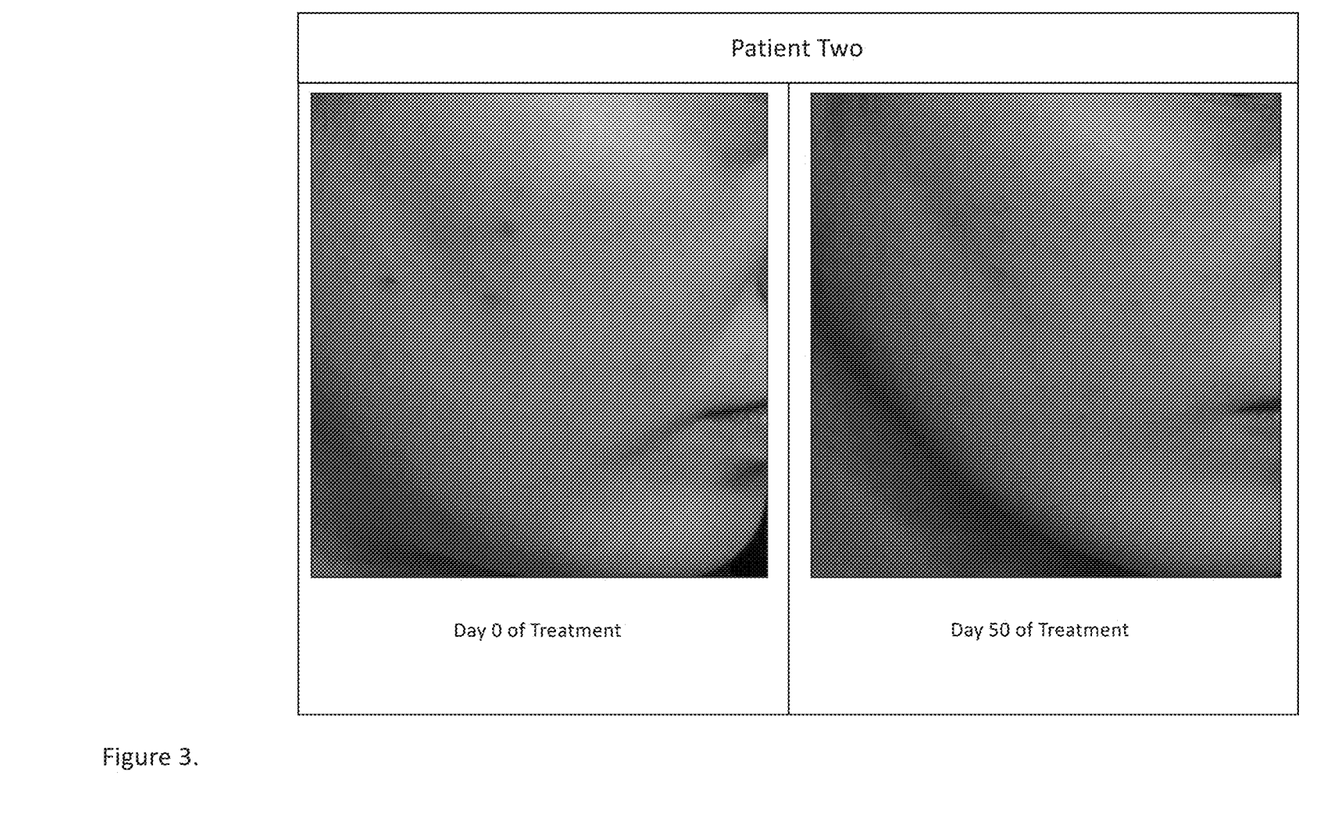
FIG. 3 is an image of the right cheek of Patient Two at time points: day 0; and, day 50; post initial day of treatment of the Topical Dermatologic Acne Treatment applied twice a day, shown consecutively from left to right, according to one embodiment of the present invention.

The present invention will now be described more fully hereinafter with reference to the accompanying images, in which preferred and other embodiments of the invention are shown. No embodiment described below limits any claimed invention and any claimed invention may cover processes or element that are not described below. The claimed inventions are not limited to products or elements having all the features of any one element or process described below or to features common to multiple or all of the elements described below. It is possible that an element or process described below is not an embodiment of any claimed invention. The applicants, inventors or owners reserve all rights that they may have in any invention claimed in this document, for example the right to claim such an invention in a continuing application and do not intend to abandon, disclaim or dedicate to the public any such invention by its disclosure in this document.

A novel Topical Dermatologic Acne Treatment Cream for use in the treatment of acne has now been developed with significant advantages over pre-existing medications. In particular, it has been found that the use of the Topical Dermatologic Acne Treatment Cream of the present invention for acne treatment results in effective treatment and reduced irritancy. In addition, it has also been discovered that the use of the Topical Dermatologic Acne Treatment Cream of the present invention significantly reduces the potential of the reoccurrence of acne when used regularly. Finally, it has been discovered that the skin revitalizing compound, an element found within the Topical Dermatologic Acne Treatment Cream, can be used as a secondary element for various skin conditions or on its own to maintain the general health and skin condition.

Treatment of the Presenting Acne

The treatment of presenting acne involves a two-stage process: 1. The treatment of presenting acne; and, 2. the conditioning of the treated skin. The treatment of the presenting acne occurs through the use of an active ingredient. The active ingredient is often a form of an antibiotic or antibacterial agent. These actives function to eliminate the bacteria on the surface of the skin which cause the formation of acne. The antibiotic or antibacterial agents often do not discriminate in their action and often cause a complete clearing of the bacterial flora found on the skin. The resultant skin lacks or has a disbalanced the microbiome that naturally protects the skin from the colonization of harmful bacteria or fungi. The flora deficient skin is often as problematic and on its own can induce acne, irritation, dryness, flakiness of the skin. The conditioning of the acne treated skin not only aids in the prevention of the colonization of harmful bacterial but also helps in maintaining the skin structure, elasticity, pH balance, to aid in the repopulation of the natural flora of the skin.

The Topical Dermatologic Acne Treatment Cream is applied to the affected areas of the skin. Often these regions include but are not limited to: the face; the neck; the shoulders; and, the back. The Topical Dermatologic Acne Treatment Cream has been found to be most effective when applied twice a day.

Bactericidal Active

The active ingredient in the Topical Dermatologic Acne Treatment Cream is BPO. The active ingredient can be interchanged with various other actives that are known to reduce the presence of acne presenting characteristics such as but not limited to: closed comedones (or "blackheads"); open comedones (or "whiteheads"); papules; cysts; nodules; and, scars (the "Presenting Acne"). The active ingredient can be described as an over the counter (OTC) and a prescription (Rx) medication. The common OTC active ingredients include but are not limited to: salicylic acid; alpha hydroxy acids; and, sulfur. Rx active ingredients are often antibiotics or other controlled substances.

The present invention is described as using BPO, but a worker skilled in the relevant would appreciate the active ingredient can be substituted or added in conjunction with BPO. BPO functions as a bactericidal and functions primarily on *Cutibacterium acnes* (formerly known as *Propionibacterium acnes*) which is a known causative agent in the formation of acne vulgaris and in Presenting Acne. BPO has been shown to be effective for acne treatment when topically applied to the affected areas in concentrations varying from 2.0-10%. In addition to BPO's action against *Cutibacterium acnes*, it acts as a mild keratolytic which helps to clear and prevent clogged pores from emerging, thereby further limiting the causative agents of the formation of acne pustules papules, whiteheads, blackheads, cysts, and, nodules.

Although shown to be an effective agent against the presenting acne pustules, is ineffective in effectively clearing acne and restoring the skin. Firstly, BPO has been shown to have the bactericidal effect on other bacterium that are often beneficial to the skin and the skin flora. This can have negative effects on the skin as colonization of harmful bacteria persists. Secondly, BPO affects the skin. BPO commonly causes initial dryness and irritation which can include, itching, crusting and swelling. The irritation affects the condition and elasticity of the skin. Thirdly, BPO, when applied to the skin, is exposed to the environment and may bleach fabric that the skin comes into contact, including clothing and/or bedding. The irritation of the skin can be reduced or eliminated if the BPO is microencapsulated, thereby limiting BPO's effect on the surface of the skin, where irritation occurs, while allowing BPO to be released at skin depths where it is most effective.

Micronized and Microencapsulated BPO

For BPO to be effective needs to penetrate the skin to the effective depth. If remaining on the surface of the skin, it cannot reach the affected area. Most issues occur within the pores of the skin, and the location of sebum production. It is at this depth that BPO is most effective at clearing the acne producing factors. These factors can be: 1. Bacteria (non-natural flora); 2. Skin imbalance; 3. Dirt and grime; and, 4. Flaking of the skin which causes the clogging the pores.

To effectively distribute BPO to the skin region of sebum production, BPO needs to be micronized. By penetrating to the sebum region of the dermis, the BPO can effectively clear of skin disease causing bacterial, such as *Cutibacterium acnes*, from all regions of the skin. To ensure the BPO penetrates to the desired depth of the skin, the BPO micronized and micro-encapsulated to prevent reformation of larger, non-penetrating BPO, while also protecting BPO from enzymatic degradation and controlling the release rate of BPO.

Another element that needs to be controlled in an effort to maintain BPO's effectiveness, is oxidation prior to its application onto the skin. One means in which BPO inhibits *Propionibacterium acnes* is through the provision of an oxygen rich environment. If BPO is oxidized prior to coming into contact with *Cutibacterium acnes* it loses this inhibitory effect. The micro-encapsulation prevents premature oxidation of BPO. As a result, the BPO is effective at inhibiting *Cutibacterium acnes* is through the provision of an oxygen rich environment. The micro-encapsulation also helps in preventing BPO bleaching fabrics it comes into contact, thereby preventing clothes and bed sheets from bleaching when worn or slept in by individuals using the Topical Dermatologic Acne Treatment Cream.

Any other active ingredient can be used in the process to either replace BPO or added with BPO for increased activity. The active ingredient can be selected from a variety of known and not yet invented. These actives include a variety of compounds described in the literature that may have an effect in reducing the presence of acne presenting characteristics. These include clinically known compounds such as: Clindamycin; Erythromycin; Minocycline; and, Dapsone. Non-traditional actives may also be used as the active. Neem oil can be used as the active acne active in case of mild to moderate acne presentation. Neem oil has been shown to have anti-bacterial properties. In addition, neem oil help in reduce and calm inflammation associated with acne. Furthermore, neem oil does not contain the properties associated with bleaching fabric that it comes into contact with. Tea Tree Oil and Zinc Salts can be used as they have been shown to reduce the presence of acne presenting characteristics. Ozone oils can also be used as an active, as its effective in clearing bacteria, vial and fungal infections while reducing inflammation and swelling. Sorbates, Parabens, and hydantoins can also be used as an active.

Use of Topical Dermatologic Acne Cream Without an Active

Topical Dermatologic Acne Treatment Cream and also be effective without the use of an active ingredient. The skin revitalizing compound has been shown to be effective in clearing mild to moderate acne. The skin revitalizing compound also aids in the reduction of the current acne in addition to reducing the potential reoccurrence of acne formation. By revitalizing and conditioning the skin, the skin revitalizing compound returns the skin to its natural homeostasis which, in turn, encourages the regrowth of natural, non-acne vulgaris causing bacterial flora of the skin. In doing so, and in reducing the drying and flaking of the skin, the skin revitalizing compound reduces the persistence of acne vulgaris. The action is two-fold, by first reducing the ability of acne-causing bacteria to flourish among the natural microbiome, and second, by reducing the clogging of the follicular canals of the skin and decreasing the oil expression linked to dryness of the skin. Furthermore, the skin revitalizing compound also normalizes the hyperkeratinisation of the skin while decreasing the sebum production, thereby revitalizing the condition of the skin.

Use of Topical Dermatologic Acne Cream with Phenolic Compounds

The effectiveness of the Topical Dermatologic Acne Treatment Cream without an Active can be further increased through the use of phenolic compounds. Phenolic compounds have been known to have positive benefits when ingested and part of the regular diet. The dietary benefits are well-known and documented through various publications and throughout the Mediterranean population. The health benefits of topical Phenolic compound are poorly understood and not researched. The effect of Phenolic compound on acne, or it's overall benefit on the skin, when used as a topical has never been determined.

Hydroxytyrosol is a Phenolic compound present in the fruit and leaf of the olive (*Olea europaea* L.), and is most commonly derived from hydrolysis of oleurpopein. Hydroxytyrosol is one of the main components of virgin olive oil, olive mill wastewater, and olive leaf extracts and is characterized by its chemical formula $C_8H_{10}O_3$. Hydroxytyrosol has been shown as a phytochemical with antioxidant found to have anti-inflammatory, antiviral, antibacterial and antifungal properties. It has also been found to improve endothelial dysfunction and decreases oxidative stress.

Hydroxytyrosol was added to the skin revitalizing compound to increase the overall effect in the reduction of the Presenting acne without the use of an Active. The resultant Topical Dermatologic Acne Cream with Hydroxytyrosol showed much improved reduction of presenting acne. The improvement matched if not surpassed the reduction of presenting acne through the use of Topical Dermatologic Acne Cream with a bactericidal active, such as BPO. As the treatment of presenting acne involves a two-stage process, that being the treatment of presenting acne, and the conditioning of the treated skin, it appears that the Hydroxytyrosol, when included in the skin revitalizing compound, provided a dual role. The dual role was observed through the increased effect of the treatment of presenting acne. Firstly, Hydroxytyrosol functioned as a bactericidal, and treated the bacteria which caused the manifestation of the presenting acne. Secondly, Hydroxytyrosol functioned to treat the skin and condition the skin by reducing inflammation and removing oxidative free radicals. Hydroxytyrosol also appeared to help nourish the skin, which was observed through the increase of general skin health and skin elasticity.

Maintenance of the Skin Upon Clearing of the Presenting Ance

The maintenance of the skin through the skin revitalizing compound is an essential element of the Topical Dermatologic Acne Treatment Cream. The clearing of the acne causing bacteria from the skin with the use of a bactericidal active has little value if the treatment cannot reduce the reoccurrence of novel acne. The immediate effect of the bactericidal active might be seen through the reduction of the presenting blackheads, whiteheads, papules, pustules, cysts, and, nodules. The immediate observable effect does not resolve the persistent issue and the cause of the skin disease.

In addition, the clearing of the acne causing bacteria from the skin is usually accompanied with irritation and reddening of the skin. Patients that are applying the bactericidal active to their affected skin in the treatment of acne often face issues of skin irritation and extreme dryness.

The skin revitalizing compound not only alleviates the issues associated with the use of bactericidal actives, but also revitalizes and conditions the skin to reduce the reoccurrence of novel acne from presenting.

The skin revitalizing compound is comprised of essential elements that help bring the skin to its natural state. The natural state reflects the condition of the skin and the flora and microbiome of the skin. The condition of the skin refers to skin elasticity/firmness/strength as well as the reduction of sebum production, the clearing of the pores, and the moisturizing and nourishing of the skin. The microbiome of the skin refers to the symbiotic bacterial flora that resides on the skin. The skin is an ecosystem, composed of living biological and physical components occupying diverse habitats. The microflora requires a stable environment in which to grow and flourish. The microflora once established prevents the acne causing bacteria from proliferating.

Condition of the Skin

To prevent the reoccurrence of the skin disease from bactericidal active treated skin requires the reduction or elimination of acne causing factors. A number of the acne causing factors are a direct result of the overall condition of the skin. The skin disease prone skin encompasses a number of these elements, which are even further exacerbated by the use of a bactericidal active. Dry skin, a common side effect of bactericidal active treatment, causes flaking of the skin cells. These flakes, or skin debris, clog the follicular canals of the skin which in turn causes the increased production of oil and sebum production. Furthermore, dry skin is also a loss of skin elasticity. The clogging of follicular canals, increased oil and sebum expression are causative agents of the skin disease.

To reduce the reoccurrence of the skin disease, the skin needs to be returned to its natural state. The elements of the skin revitalizing compound reduce or eliminate the acne causing factors. The elements help increase the skin elasticity, skin firmness, reduce sebum production, and increase the moisture of the skin cells.

The Skin Ecosystem

The skin ecosystem is comprised of 1.8 m² of diverse habitats with an abundance of folds, invaginations and specialized niches that support a wide range of microorganisms. As such, different niches have different and diverse milieu of microorganisms which forms a microbiome. Furthermore, the age of the individual and hormone expression dramatically alters the diverse milieu of the microbiome. These microorganisms include: bacteria, fungi, viruses and mites. The microorganisms form communities that are deeply intertwined. A majority of the microorganisms are harmless and in some cases provide vital functions that aid the health and vitality of the skin. Symbiotic microorganisms occupy a wide range of skin niches and protect against invasion by more pathogenic or harmful organisms, of which can cause acne vulgaris. Disruptions in the balance of the microorganism ecosystem or the host-microorganism relationship can result in skin disorders, infections, and the emergence of the skin disease. Conversely, the return of the balance of the microbiome, can result in the protection against pathogenic or harmful disorders that are known to be causative agents of the skin disease.

The microorganisms within the ecosystem work in concert and work in a cooperative manner within the niche of the skin that they inhabit. The topology of the skin, the skin temperature, the pH balance, and density of hair follicles and glands affect the microenvironment. The expression of hormones, the age of the skin can also affect the microenvironment and the microflora. The composition of the dermal microflora varies from site to site and throughout the life span of the individual, according to the characteristics of the microenvironment. Skin sites with partial occlusion harbor more microorganisms than do less occluded areas. Differences relate to the increased amount of moisture, higher body temperature, greater concentration of skin surface lipids, and hormone expression.

Disruption in the balance can occur as a result of endogenous or exogenous factors. Endogenous factors can include skin and microorganism genetic variation, which selects for specific microbial communities, thereby altering the ecosystem and inducing an imbalance that affects the health of the skin. Exogenous facts include washing and the type of habits of the of the individual, including but not limited to: the amount of exercise, the diet; environmental factors.

The current understanding of microflora is not clear. The location of the microflora on the skin provides the first misunderstanding of the microflora. In addition to various locations along the body, the specific portion of the skin can also have a diverse microorganisms residing within specific locations. For example, the skin the microorganisms live in the superficial layers of the stratum corneum and in the upper parts of the hair follicles, while other bacteria reside in the deeper areas of the hair follicles and in areas beyond the reach of ordinary disinfection procedures. These bacteria form a reservoir for recolonization after the surface bacteria are removed.

The Need for Reconditioning of the Skin

The current treatment methods do not attempt to re-establish the flora and the microbiome. They aim to eliminate the bacteria on the surface of the skin. The problem with this type of treatment is that if does not repopulate natural microbiome and flora. As a result, the skin post-treatment, is vulnerable to the repopulation of various microorganisms then the skin will be susceptible to the repopulation of the skin disease causing bacteria, including but not limited to, non-symbiotic and destructive bacteria. This type of bacteria, once a resident on the surface of the skin, and the superficial layers of the stratum corneum, will prohibit the symbiotic bacteria from populating and thereby inhibiting the natural flora to re-establish. As such, the patient using the current treatment system will be in a constant cycle of treatment and constant reestablishment of the skin disease. Furthermore, the non-symbiotic bacteria will irritate and inflame the skin thereby further increasing the phenotypic effect of the skin disease.

Skin Revitalising Compound

The conditioning and revitalization of the skin is accomplished through the skin revitalizing compound. The skin revitalizing compound is comprised of elements that condition the skin and aid in repopulating the natural flora and microbiome of the skin. Each element of the skin revitalizing compound functions in concert to aid in the skin conditioning while providing nutritional and native ground for the repopulation of the natural flora and microbiome. The elements of the skin reconditioning compound are no-active and, on their own, cannot reconstitute the natural flora of the skin. The elements included in the skin revitalizing compound include: retinoid; bakuchiol; green tea extract green coffee extract; epilobium fleischeri extract; *glycine soja* fatty acids; citric acid; dimethicone; pentaerythrityl tetracaprylate; and, niacinamide.

Retinoid

Retinoid, a vitamin A derivative has been proven to boost collagen production while unclogging pores. The unclogging of pores allows other elements found in the skin revitalizing compound to penetrate the pores and have an increased effectiveness. Retinoid has also been shown to reduce skin sebum production and reduce inflammation. Retinoid has also been shown to increase collagen skin production which rejuvenates the skin. It has also been shown to stimulate blood vessel production and can regulate growth and differentiation of the keratinocytes preventing pre-cancer skin conditions such as actinic keratosis. The concentration of retinoid in the skin revitalizing compound can be anywhere between 0.2-2.00% w/w. In the preferred embodiment, retinoid is at 0.5% w/w. In the more preferred embodiment, the retinoid is provided as a retinol-retinaldehyde mixture with a total concentration between 0.2-2.00% w/w. The retinoid can be provided in its various and known states, formations and structures. A worker skilled in the relevant art would appreciate the various forms and structures of retinol and its derivative can be used interchangeable and based on the specific need for reduction of skin irritation while maintaining optimal effectiveness. A worker skilled in the relevant art would appreciate that the retinoid can be provided in various forms, including but not limited to: retinol; retinaldehyde; retinyl palmitate; adapalene; isotretinoin; tretinoin; and, tazarotene.

Bakuchiol

Bakuchiol is a naturally occurring antioxidant found in the seeds of Psoralea Corylifolia. When applied to this skin bakuchiol can lead to the increased production of collagen and reduction of inflammatory mediators. It has also been shown to have antioxidant properties. Bakuchiol increases cell turnover and in doing so decreases skin laxity and overall photodamage. It has been linked to increase elasticity, firmness, and decrease pigmentation. The concentration of bakuchiol in the skin revitalizing compound can be anywhere between 0.2-2.00% w/w. In the preferred embodiment, bakuchiol is at 0.5% w/w.

Green Coffee Bean Extract

Green coffee bean extract is a naturally occurring antioxidant. It is an effective means of boosting collagen production in the skin which has been found to rejuvenate the skin. Green coffee bean extract has also shown to increase the firmness of the skin while improving redness and overall texture. In addition, Green coffee bean extract is a great skin moisturizer. The concentration of green coffee bean extract in the skin revitalizing compound can be anywhere between 0.2-2.00% w/w. In the preferred embodiment, green coffee bean extract is at 0.5% w/w.

Green Tea Extract

Green tea extract is a naturally occurring antioxidant. It is an effective means of boosting collagen production in the skin which has been found to rejuvenate the skin. Green tea extract has also shown to increase the firmness of the skin while improving redness, elasticity and overall texture. In addition, Green tea extract is a great skin moisturizer. The concentration of green tea extract in the skin revitalizing compound can be anywhere between 0.2-2.00% w/w. In the preferred embodiment, green tea extract is at 0.5% w/w.

Epilobium Fleischeri Extract

Epilobium Fleischeri extract is a naturally occurring antioxidant. It is found in the Epilobium Fleischeri, a rare Alpine species of plant. It is rich in flavonoids, which have anti-inflammatory properties. Furthermore, Epilobium Fleischeri extract is beneficial to oily skin as it regulates production of sebum. The concentration of Epilobium Fleischeri extract in the skin revitalizing compound can be anywhere between 0.2-2.00% w/w. In the preferred embodiment, Epilobium Fleischeri extract is at 0.5% w/w.

*Glycine Soja* Fatty Acid

*Glycine Soja* fatty acid is obtained from the Soybean. *Glycine Soja* fatty acid is comprised of a mixture of mono, di-, and triglycerides as well as a variety of fatty acids. It operates as an antioxidant and as a skin-conditioning agent in both forms, as an emollient and an occlusive. The concentration of *Glycine Soja* fatty acid in the skin revitalizing compound can be anywhere between 0.2-2.00% w/w. In the preferred embodiment, *Glycine Soja* fatty acid is at 0.5% w/w.

Citric Acid

Citric acid is a common element found in many fruits. Its effect on the skin included improving the overall texture and lightening the overall skin tone. Citric acid can also restrict the production of melanin, which has been found responsible for skin blemishes. Furthermore, citric acid is a form of alpha-hydroxy acid (AHA), which exfoliates the skin, thereby further rejuvenating the overall condition of the skin. As an acid, it also balances the overall pH of the skin. The concentration of citric acid in the skin revitalizing compound can be anywhere between 0.05-1.00% w/w. In the preferred embodiment, citric acid is at 0.1% w/w.

Dimethicone

Dimethicone is a form of silicone. It acts as a skin condition agent both as an emollient and an occlusive. It is also known for its skin protectant abilities. The concentration of Dimethicone in the skin revitalizing compound can be anywhere between 0.5-3.00% w/w. In the preferred embodiment, Dimethicone is at 1.0% w/w.

Pentaerythrityl Tetracaprylate

Pentaerythrityl Tetracaprylate acts as a skin conditioning agent through its action as an emollient. It also acts as a protective barrier on the skin thereby preventing moisture loss. The concentration of Pentaerythrityl Tetracaprylate in the skin revitalizing compound can be anywhere between 0.5-3.00% w/w. In the preferred embodiment, Pentaerythrityl Tetracaprylate is at 2.0% w/w.

Niacinamide

Niacinamide is an effective skin repairing element. It can increase skin hydration, brighten skin tone, and improve skin texture and structure, elements that are key for skin rejuvenation. It may also reduce overall sebum skin production, thereby making the skin less oily and pores less likely to clog. Niacinamide has also a stabilizing effect on epidermal barrier function and has anti-inflammatory properties. The concentration of Niacinamide in the skin revitalizing compound can be anywhere between 0.5-3.00% w/w. In the preferred embodiment, Niacinamide is at 2.0% w/w.

Additional Elements

Additional elements, also known as aid elements, help improve the effectiveness of the skin revitalizing compound. The aid elements aid in the mode of action of the skin retivalizing compound. They act in a manner that aids in the binding, protection, and placement of the elements of the conditioning complex on the affected areas of the skin. They may also aid in the prevention of evaporation of the conditioning complex while on the surface of the skin. The aid elements include but are not limited to: phospholipids; glycolipids; eicosene copolymer; propylene glycol; sodium benzoate; hydroxypropyl methylcellouse;

Microflora was not used in the conditioning complex as the microflora changes between the various regions of the skin along with the various ages of individuals afflicted with the skin disease and the hormone expression profiles. Moisture, temperature, and exposure to the sun and air exposure help shape the various microflora of the skin. As does the age of the individual and their corresponding hormone expression levels. As such, the type of microflora found on the forehead will vary from the type of microflora found in the armpit. The microflora found on the forehead of a 14-year-old boy will be different from that of the forehead of a 38 year old woman. The skin structure, pH balance is dramatically different between various age groups. The key element of repopulating the appropriate microflora is to ensure an optimum environment and skin conditioning.

Effectiveness

The Topical Dermatologic Acne Treatment Cream is effective at reducing or eliminating most of the characteristic of the skin disease. After a treatment of twenty-five (25) to fifty (50) days, patient saw a dramatic reduction in the presence of: blackheads; whiteheads; papules; pustules; cysts; nodules; and scars. Furthermore, the patents also observed an increase in the general health and condition of their skin. Patients indicated that their skin felt better, was less oily, and appeared to have less inflammatory lesions, "white" and "black" heads with a smoother and even skin tone.

Patient Example 1

The Topical Dermatologic Acne Treatment Cream was used by two women aged 25-30 years old (the "subjects").

The subjects skin condition prior to the use of the Topical Dermatologic Acne Treatment Cream was poor. The subjects both presented with various acne inflammatory lesions including papules, pustules, cysts, nodules, scars along with whiteheads throughout cheek, chin jawline and neck. Prominent acne papules and pustules were visible on the cheek and on the chin. The subjects applied a thin layer of the Topical Dermatologic Acne Treatment Cream on their face twice daily, once in the morning and once at night. The subjects maintained their regular daily routine. The treatment lasted for 50 days. Prior to using the Topical Dermatologic Acne Treatment Cream, one of the subjects was on various over the counter and prescription acne medication. The subject has even tried hormonal modifiers to alleviate the continual reoccurrence of acne.

Results

The assessment post proposed acne treatment regimen revealed significant (>50%) reduction in a number of inflammatory and noninflammatory acne lesions. Also, the Overall Clinical Assessment showed a decrease score from 3 to 1. The subjective assessment of the treatment showed great satisfaction with the treatment. The objective assessment revealed significant decrease in the number of inflammatory papules, open and closed conmedones, and postinflammatory dyschromias.

Patient Example 2

The Topical Dermatologic Acne Treatment Cream was used by a middle-aged man (the "patient"). The patient exhibited a lesion on his upper left cheek that resembled actinic keratoses. The skin lesion appeared pinkish-red and contained visible rough scaling round the lower region. The general look of the lesion was thick, scaly and felt dry and very rough with a diameter of approximately eight (8) millimeters. The patient applied a thin layer of the Topical Dermatologic Acne Treatment Cream on his face twice daily, once in the morning and once at night. The patient maintained his regular daily routine. The treatment lasted for 50 days.

Results

The assessment post proposed acne treatment regimen revealed significant reduction in the appearance of the lesion. The lesion appeared smaller, with a smoother and moisturized texture. The scaling and rough spots around the edge were significantly reduced. The lesion was almost unnoticeable on the cheek. The subjective assessment of the treatment showed great satisfaction with the treatment.

Patient Example 3

The Topical Dermatologic Acne Treatment Cream with Hydroxytyrosol and no Active was used by a twenty-six year old female (the "patient"). The patient exhibited a newly acquired inflammatory and noninflammatory acne lesions on her cheek and forehead. The patient presented with various acne inflammatory lesions including papules, pustules, cysts, nodules, scars along with whiteheads throughout cheek, and forehead. Prominent acne papules and pustules were visible on the cheek. The patient had an oily skin composition. The patient indicated that her skin was previously clear and that she started noticing acne lesions upon reaching the age of twenty-six. The patient applied a thin layer of the Topical Dermatologic Acne Treatment Cream with Hydroxytyrosol and no Active on her face twice daily, once in the morning and once at night. The patient maintained this as her regular daily routine. The treatment lasted for twenty-five days.

Results

The assessment post proposed acne treatment regimen revealed significant reduction in the appearance of the lesion. After fourteen days, the patient's skin was completely clear of any acne lesions on her check and forehead. Her skin appears noticeably less oily and healthy. This skin maintained throughout the remaining eleven days of the treatment. The subjective assessment of the treatment showed great satisfaction with the treatment.

Patient Example 4

The Topical Dermatologic Acne Treatment Cream with Hydroxytyrosol and no Active was used by a pre-teen female 10 years old (the "patient"). The patient skin condition prior to the use of the Topical Dermatologic Acne Treatment Cream with Hydroxytyrosol and no Active was poor. The patient presented with various acne inflammatory lesions including papules, pustules, cysts, nodules, throughout cheek, and chin jawline. Prior to enrolling in the treatment, the patient was prescribed and was actively using tactupump. The patient discontinued her use of the tactupump prior to enrolling in the treatment. The patient applied a thin layer of the Topical Dermatologic Acne Treatment Cream on their face twice daily, once in the morning and once at night for fifty (50) days. The patient maintained their regular daily routine. The routine was reduced to once a day upon a significant clearing of the skin.

Results

The assessment post proposed acne treatment regimen revealed significant (>60%) reduction in a number of inflammatory and noninflammatory acne lesions. Also, the Overall Clinical Assessment showed a decrease score from 3 to 1. The subjective assessment of the treatment showed great satisfaction with the treatment. The objective assessment revealed significant decrease in the number of inflammatory papules, open and closed conmedones.

Method of Manufacture of the Topical Dermatologic Acne Treatment Cream

The Topical Dermatologic Acne Treatment Cream is comprised to two main elements, the bactericidal and the skin revitalizing compound. As a result, the method of manufacture comprises of steps that build the bactericidal and the skin revitalizing compound separately, then combining them in a single soluble compound. The manufacture of the bactericidal and skin revitalizing compound individually allows for the skin revitalizing compound to be used alone, or in association with other elements, for other skin indications. The skin revitalizing compound can be used alone to function as a daily moisturizer and skin conditioner to maintain the general health of the skin. Furthermore, the skin revitalizing compound can be incorporated with various actives to treat various skin indications. The skin indications and corresponding to the use of the skin revitalizing compound, and the associated active include, but are not limited to: rosacea—sulphur; demodicosis—*chrysanthemum* extract melasma—hydroquinone; and skin rejuvenation—ascorbic acid.

The method of manufacture of the Topical Dermatologic Acne Treatment Cream comprises of a heated oil in water blended emulsion with temperature sensitive materials that are added and blended as the heated oil gradually decreased in temperature. The Topical Dermatologic Acne Treatment Cream can also be produced in a water in oil emulsion, a liquid, a suspension, a water based gel, a hydro alcoholic gel, an ointment, and encapsulated powder or micro sponges, as a transdermal system and a film forming application.

In summary, the present invention provides a topical cream composition for the treatment of acne vulgaris and the method of manufacturing thereof. The topical dermatologic acne treatment cream functions through a two-stage process: the clearing the acne currently present on the skin; and reducing the potential reoccurrence of additional acne. The clearing of the presenting acne is accomplished through the use of an acne bactericidal. The reducing the potential reoccurrence of additional acne is accomplished through a skin revitalizing compound that returns the skin to its natural homeostasis thereby encouraging the regrowth of natural, non-acne vulgaris causing, bacterial flora and the microbiome of the skin. The present invention also provides for a method of manufacture the Topical Dermatologic Acne Treatment Cream through two-stage process wherein the bactericidal is added to the skin revitalizing compound. The skin revitalizing compound can be used as a secondary element to various skin conditions or on its own to maintain the general health and skin condition.

What is claimed is:

1. A method of improving appearance of topical dermatologic acne skin, the method comprising:
    identifying a target portion of skin that includes topical dermatologic acne;
    providing a dermatologic acne treatment cream comprising a micro-encapsulated active ingredient and a skin revitalizing complex; wherein the micro-encapsulated active ingredient reduces inflammation, reduces oxidative free radicals, and decreases oxidative stress, and the skin revitalizing complex revitalizes and conditions the skin; wherein the micro-encapsulated active ingredient also functions to reduce inflammation and preventing pre-cancerous skin conditions, while the skin revitalizing complex assists in skin elasticity by boosting collagen production;
    daily topical application of the dermatologic acne treatment cream, to the target portion of the skin for six weeks to allow the dermatologic acne treatment cream to noticeably reduce the topical dermatologic acne; and
    continued daily topical application of the dermatologic acne treatment cream to the target portion of the skin to reduce a chance of reoccurrence of the topical dermatologic acne.

2. A method of improving appearance of actinic keratosis, the method comprising:
    identifying a target portion of the skin that includes actinic keratosis;
    providing a dermatologic acne treatment cream comprising a micro-encapsulated active ingredient and a skin revitalizing complex; wherein the micro-encapsulated active ingredient reduces inflammation, reduces oxidative free radicals, and decreases oxidative stress, and the skin revitalizing complex revitalizes and conditions the skin; wherein the micro-encapsulated active ingredient also functions to reduce inflammation and preventing pre-cancerous skin conditions, while the skin revitalizing complex assists in skin elasticity by boosting collagen production; and,
    daily topical application of the dermatologic acne treatment cream, to the target portion of the skin for six weeks to allow the dermatologic acne treatment cream to noticeably reduce actinic keratosis.

3. A method of improving appearance of acne scarring, the method comprising:
    identifying a target portion of skin that includes acne scarring;
    providing a dermatologic acne treatment cream;
    daily topical application of a dermatologic acne treatment cream to the target portion of the skin for six weeks to allow the dermatologic acne treatment cream to noticeably reduce the appearance of acne scarring; and,
    continued daily topical application of the dermatologic acne treatment cream to the target portion of the skin to reduce a chance of reoccurrence of the acne scarring;
    wherein said acne treatment cream comprises:
        a micro-encapsulated active ingredient; and a skin revitalizing complex;
        wherein the micro-encapsulated active ingredient reduces inflammation, reduces oxidative free radicals, and decreases oxidative stress, and the skin revitalizing complex revitalizes and conditions the skin; wherein the micro-encapsulated active ingredient also functions to reduce inflammation and preventing pre-cancerous skin conditions, while the skin revitalizing complex assists in skin elasticity by boosting collagen production.

4. The method of improving appearance of topical dermatologic acne skin of claim 1 wherein the skin revitalizing complex comprises:
    a) niacinamide;
    b) retinol;
    c) bakuchiol;
    d) green coffee bean extract;
    e) green tea extract;
    f) epilobium fleischeri extract;
    g) citric acid;
    h) dimethicone; and
    i) pentaerythrityl tetracaprylate;
    wherein elements of the skin revitalizing complex restores natural elasticity and oil production of the skin, which functions as an antioxidant, decreases sebum production, increases collagen formation, and provides necessary conditioning of the skin to provide for natural skin flora and microbiome to repopulate and flourish on a surface of the skin.

5. The method of improving appearance of topical dermatologic acne skin of claim 1, wherein said active ingredient comprises tea tree oil.

6. The method of improving appearance of topical dermatologic acne skin of claim 1, wherein said active ingredient comprises zinc salts.

7. The method of improving appearance of topical dermatologic acne skin of claim 1, wherein said active ingredient comprises Hydroxytyrosol.

8. The method of improving appearance of topical dermatologic acne skin of claim 1, wherein said cream aids in repopulation of natural skin flora and microbiome.

9. The method of improving appearance of topical dermatologic acne skin of claim 1, wherein said active ingredient comprises neem oil.

10. The method of improving appearance of actinic keratosis of claim 2 wherein the skin revitalizing complex comprises:
    a) niacinamide;
    b) retinol;
    c) bakuchiol;
    d) green coffee bean extract;
    e) green tea extract;
    f) epilobium fleischeri extract;

g) citric acid;
h) dimethicone; and
i) pentaerythrityl tetracaprylate;
wherein elements of the skin revitalizing complex restores natural elasticity and oil production of the skin, which functions as an antioxidant, decreases sebum production, increases collagen formation, and provides necessary conditioning of the skin to provide for natural skin flora and microbiome to repopulate and flourish on a surface of the skin.

11. The method of improving appearance of acne scarring of claim 3 wherein the skin revitalizing complex comprises:
a) niacinamide;
b) retinol;
c) bakuchiol;
d) green coffee bean extract;
e) green tea extract;
f) epilobium fleischeri extract;
g) citric acid;
h) dimethicone; and
i) pentaerythrityl tetracaprylate;
wherein elements of the skin revitalizing complex restores natural elasticity and oil production of the skin, which functions as an antioxidant, decreases sebum production, increases collagen formation, and provides necessary conditioning of the skin to provide for natural skin flora and microbiome to repopulate and flourish on a surface of the skin.

12. The method of improving appearance of actinic keratosis of claim 2, wherein said active ingredient comprises tea tree oil.

13. The method of improving appearance of acne scarring of claim 3, wherein said active ingredient comprises tea tree oil.

14. The method of improving appearance of actinic keratosis of claim 2, wherein said active ingredient comprises zinc salts.

15. The method of improving appearance of acne scarring of claim 3, wherein said active ingredient comprises zinc salts.

16. The method of improving appearance of actinic keratosis of claim 2, wherein said active ingredient comprises Hydroxytyrosol.

17. The method of improving appearance of acne scarring of claim 3, wherein said active ingredient comprises Hydroxytyrosol.

18. The method of improving appearance of actinic keratosis of claim 2, wherein said cream aids in repopulation of natural skin flora and microbiome.

19. The method of improving appearance of acne scarring of claim 3, wherein said cream aids in repopulation of natural skin flora and microbiome.

20. The method of improving appearance of actinic keratosis of claim 2, wherein said active ingredient comprises neem oil.

21. The method of improving appearance of acne scarring of claim 3, wherein said active ingredient comprises neem oil.

* * * * *